United States Patent [19]

Kurek

[11] Patent Number: 4,482,741

[45] Date of Patent: Nov. 13, 1984

[54] PREPARATION OF XYLYLENEDIAMINE

[75] Inventor: Paul R. Kurek, Schaumburg, Ill.

[73] Assignee: UOP Inc., Des Plaines, Ill.

[21] Appl. No.: 569,367

[22] Filed: Jan. 9, 1984

[51] Int. Cl.$^3$ ............................................. C07C 85/12
[52] U.S. Cl. .................................................. 564/415
[58] Field of Search ........................................ 564/415

[56] References Cited

U.S. PATENT DOCUMENTS

| | | | |
|---|---|---|---|
| 3,255,248 | 6/1966 | Suessenguth et al. | 564/415 X |
| 3,284,483 | 11/1966 | Erner | 564/415 X |
| 3,728,284 | 4/1973 | Reynolds | 564/415 X |
| 4,254,059 | 3/1981 | Grey et al. | 564/415 X |

FOREIGN PATENT DOCUMENTS 852972 11/1960 United Kingdom.
1149251 4/1969 United Kingdom.

*Primary Examiner*—Paul F. Shaver
*Attorney, Agent, or Firm*—William H. Page, II; Raymond H. Nelson

[57] ABSTRACT

Xylylenediamines may be prepared by reducing the corresponding phthalonitrile with hydrogen in the presence of a catalyst comprising cobalt promoted with titanium composited on a solid support with the added presence of ammonia. By utilizing this particular catalyst with ammonia and a solvent comprising a xylylenediamine, it is possible to effect the reduction at temperatures in the range of from about 80° to about 125° C. and at a pressure not greater than 1000 psig. By utilizing various components of the system it is possible to attain yields of the desired product in excess of 90%.

13 Claims, No Drawings

PREPARATION OF XYLYLENEDIAMINE

BACKGROUND OF THE INVENTION

Xylylenediamines such as m-xylylenediamine and p-xylylenediamine are compounds which are useful as chemical intermediates in the plastic and polymer fields. These compounds may be prepared from the isomeric phthalonitriles such as isophthalonitrile or terephthalonitrile utilizing nickel catalysts or other metallic hydrogenation catalysts at elevated temperatures and pressures. However, the reduction reaction is effected with some degree of difficulty due to the formation of undesirable side products resulting from a partial reduction, a polymerization or cleavage of the starting product.

One method of effecting the hydrogenation of the phthalonitrile compounds is set forth in British Patent Specification No. 1,149,251 in which aromatic dinitriles are hydrogenated in the presence of a catalyst comprising a zirconium-promoted cobalt catalyst in the presence of ammonia. The solvent which is employed to effect the reaction has been conventionally described as aromatic hydrocarbons, aliphatic alcohols, aliphatic hydrocarbons, dimethylformamide, dioxane, etc. The reaction is described as being effected at temperatures which will be low enough to maintain the ammonia in the liquid phase such as from about 60° to about 130° C. and pressures of from about 1000 to about 5000 pounds per square inch gauge (psig). The preferred operating conditions as described in this patent include temperatures ranging from 110° to 130° C. and reactor pressures ranging from 1500 to 2500 psig. However, the use of the conditions described would lead to a vaporization of the solvents and ammonia, thus causing an amine cleavage with the resulting formation of methylbenzyl amines.

Another British Pat. No. 852,972, also discloses a process for the production of xylylenediamines. This patent teaches that the hydrogenation of phthalonitriles is accomplished in the presence of cobalt catalysts containing chromium and/or manganese. In addition, the catalyst also contains a pyro or poly form of an acid such as phosphoric acid, sulfuric acid, boric acid, etc. The hydrogenation reaction which is taught in this patent utilizes relatively high pressures ranging from about 1470 to about 7350 psig and preferably at 4410 psig. The use of such a high pressure is in contrast to the relatively low pressures utilized in the present invention, that is, pressures less than 1000 psig.

As will hereinafter be shown in greater detail, it has now been discovered that by employing a catalyst comprising cobalt promoted with titanium, composited on a solid support, as well as a xylylenediamine as a solvent for the reaction, it is possible to effect the reduction of a phthalonitrile at a relatively low pressure with a minimum formation of any undesired side products and a correspondingly greater yield of the desired product.

BRIEF SUMMARY OF THE INVENTION

This invention relates to a process for the preparation of xylylenediamines. More specifically, the invention is concerned with an improvement in a process for the preparation of xylylenediamines by the reduction of the corresponding phthalonitriles utilizing as a solvent therefore, certain compounds which will facilitate and enhance the reaction. By utilizing the particular reaction conditions and components of the reaction mixture, it will be possible to obtain enhanced yields of the desired products, with a corresponding decrease in the amount of unwanted side products which may form during the reaction.

It is therefore an object of this invention to provide an improved process for the production of xylylenediamines.

In one aspect an embodiment of this invention resides in a process for the preparation of a xylylenediamine which comprises treating a phthalonitrile with hydrogen in the presence of ammonia and a catalyst comprising cobalt promoted with titanium composited on a solid support, said treatment being effected in the presence of a solvent comprising a xylylenediamine and recovering the resultant xylylenediamine.

A specific embodiment of this invention will be found in a process for the preparation of m-xylylenediamine which comprises treating isophthalonitrile with hydrogen at a temperature in the range of from about 80° to about 125° C. and a pressure in the range of from about 900 to about 1000 psig in the presence of ammonia and a catalyst comprised of cobalt promoted with titanium composited on kieselguhr in a solvent medium comprising m-xylylenediamine, and recovering the resultant m-xylylenediamine.

Other objects and embodiments will be found in the following further detailed description of the invention.

DETAILED DESCRIPTION OF THE INVENTION

As hereinbefore set forth, the present invention is concerned with the preparation of xylylenediamines and particularly encompasses the use of certain reaction conditions and solvent to minimize loss of product.

Various aspects of the reduction reaction in which a phthalonitrile is reduced to the corresponding xylylenediamine must be taken into consideration when effecting the desired process. For example, the phthalonitriles exhibit poor solubility in many common solvents and when attempting to utilize a continuous process, it is necessary that the feedstock be completely soluble in the reaction medium. In addition, the reduction of the phthalonitrile with hydrogen may, if care is not taken, result in unwanted side reactions such as polymerization to give dimers or cleavage of the amine groups to give methylbenzyl amines and/or xylenes.

It is known that the presence of ammonia in the reaction medium tends to minimize the aforesaid undesired reactions of polymerization and cleavage. However, the ammonia must be present in the liquid phase inasmuch as if the ammonia is present in a gaseous phase, the effect of its presence will be nullified. In addition, not all of the well-known reduction catalysts are effective in the reduction of the phthalonitriles with hydrogen to form the desired xylylenediamines. For example, nickel composited on kieselguhr, ruthenium composited on carbon, platinum composited on carbon, palladium composited on carbon, rhenium composited on alumina, etc. are relatively ineffective in promoting the reduction to the desired product. It is therefore necessary to utilize a heterogeneous catalyst which will possess the desired activity. In addition, the solid support upon which the catalytic metal is composited also affects the activity of the catalyst and its ability to sustain a continued conversion of the feedstock to the desired product.

Another critical element which is present in the process for producing xylylenediamines comprises the choice of solvent in which the reduction reaction is effected. Conventional organic solvents usually possess some disadvantages which may lead to deleterious effects in the present process. For example, a solvent such as 2-methoxyethanol is readily available and as been used in other reduction processes. However, the phthalonitriles have a limited solubility in this solvent and may not be employed in continuous processings. For example, phthalonitriles are relatively insoluble or only partially soluble in such well-known solvents as ethyl acetate, ethylene glycol, isopropyl alcohol, methanol, p-dioxane, toluene, etc. Another solvent which is widely used in organic processes comprises acetone. Although the phthalonitriles are soluble in acetone, this solvent may not be employed inasmuch as it would be hydrogenated to isopropyl alcohol and in addition would form ketimines with the xylylenediamine products. A further limitation on the selection of a solvent resides in the boiling point thereof. In order to effect the desired reduction, it is necessary that the solvent which is chosen exist as a liquid within the range of the reaction temperature.

As was hereinbefore set forth, ammonia has been used in the reduction of phthalonitriles as a protection against the cleavage of the amine group from the benzyl moiety and, in addition, minimizes the formation of secondary and tertiary amine polymers. However, ammonia must be in the liquid phase in order to operate efficiently as the protecting agent.

It has now been discovered that all of the drawbacks of reducing a phthalonitrile to the corresponding xylylenediamine may be overcome and yields consistently in excess of 90% of the desired product obtained when utilizing the process of the present invention.

This process involves the treatment of a phthalonitrile such as m-phthalonitrile or p-phthalonitrile with hydrogen in the presence of a catalyst comprised of cobalt promoted with titanium composited on an inert support at reaction conditions. The reaction conditions which are employed to effect the desired reduction will include temperatures in the range of from about 80° to about 125° C. and pressures not greater than 1000 psig, the preferred pressure range being from about 900 to about 1000 psig. The solvent medium in which the reaction is effected comprises a xylylenediamine such as m-xylylenediamine or p-xylylenediamine. By utilizing this particular solvent in which the reaction is effected, it has been found that several advantages are afforded. Among these advantages are included the fact that the xylylenediamine will act as a quench for any exotherms which have been generated during the reduction process, will eliminate the requirement for an additional solvent in the process which is needed for the blending and solubility of the phthalonitrile, will improve the recovery of the product, will minimize the deactivation of the catalyst, and as the most important advantage, solubilize the ammonia which again is an important factor or parameter in maximizing the yield of the desired product. As an added advantage, it will also permit the reaction to be effected at a lower pressure, that is, not greater than 1000 psig, thus solubilizing the ammonia to a greater extent into the liquid phase with the attendant advantages hereinbefore set forth. In addition, an added benefit which results when operating the reaction at pressures less than about 1000 psig in a continuous process is found in the fact that high pressure equipment normally utilized in this particular reduction reaction is not required. Therefore, there will be lower capital expenditures permitting a more favorable economical operation of the process and concurrently negating the hazards which are usually associated with the use of high-pressure ammonia.

The catalyst which is used to effect this reaction comprises a cobalt promoted with titanium composited on an inert support. The titanium will be present in the catalyst in an amount in the range of from about 1% to about 20% by weight of the catalyst, while the cobalt is present in said catalyst in an amount in the range of from about 40% to about 70% by weight of the catalyst. Examples of inert supports upon which the cobalt promoted with titanium may be composited will include carbon, charcoal, diatomaceous earth, kieselguhr, montmorillonite, bentonite, silica, etc. As will hereinafter be shown in greater detail, this catalyst will possess an improved operating life as evidenced by a resistance to deactivation in a recycle operation when compared to prior catalysts comprising cobalt promoted with zirconium.

The processes of the present invention may be effected in any suitable manner and may comprise either a batch or continuous type operation. For example, when a batch type operation is employed, a quantity of the catalyst comprised of cobalt promoted with titanium composited on a solid support along with the solvent comprising xylylenediamine and ammonia is placed in a pressure vessel such as an autoclave along with the phthalonitrile which is to be reduced. Preferably the catalyst, solvent and phthalonitrile are charged, the vessel sealed and ammonia is charged in by weight. The autoclave is then pressured to the desired operating pressure with hydrogen, said pressure being not greater than 1000 psig. Following this, the autoclave is heated to the desired operating temperature and maintained thereat for a predetermined period of time which may range from about 0.5 up to about 10 hours or more in duration. During the reaction period the pressure is maintained at the desired operating level by the addition of hydrogen on demand. At the end of the reaction period, heating is discontinued and after the autoclave has returned to room temperature any excess pressure which is present is vented and the autoclave is opened. The reaction mixture is recovered, separated from the catalyst by conventional means such as filtration, decantation, etc. and subjected to further separation means whereby the desired xylylenediamine is separated from any unreacted starting material and/or unwanted side reaction products which may have formed during the reaction, and recovered.

It is also contemplated within the scope of this invention that the reduction of the phthalonitrile to the corresponding xylylene diamine may be effected in a continuous manner or operation. The continuous process may be effected by charging the phthalonitrile which is to undergo reduction to a reaction zone containing the aforesaid catalyst and solvent. In addition, ammonia is also continuously charged to the reaction zone along with the hydrogen necessary for the reductive process. Alternatively, the phthalonitrile, ammonia, and xylylenediamine solvent may be mixed and charged to the reactor. After passage through the reaction zone for a predetermined period of time, the reactor effluent is continuously withdrawn and subjected to conventional means of separation such as distillation whereby the desired xylylenediamine product is separated from unreacted phthalonitrile and side products while a portion of the product effluent is recycled back to the reactor zone to form a portion of the feedstock.

The physical form of the catalyst which is employed in this reduction process will enable various types of continuous processes to be employed. One type of continuous process which may be used comprises a fixed bed type of operation in which the catalyst is disposed as a fixed bed in the reaction zone and the various components of the reaction are passed through the catalyst bed in either an upward or downward flow. Another type of continuous process which may be employed comprises the moving bed type of operation in which the catalyst and reactants are passed through the reaction zone either concurrently or countercurrently to each other. Alternatively, a third type of operation may be employed in which the catalyst is carried into the reaction zone as a slurry in either the phthalonitrile or the xylylenediamine solvent which is present in said zone.

The following examples are given for purposes of illustrating the advantages of utilizing the particular type of catalyst and solvent which are employed in the reductive reaction whereby the phthalonitrile is converted to the corresponding xylylenediamine. However, it is to be understood that these examples are merely illustrative in nature and that the present process is not necessarily limited thereto.

EXAMPLE I

To illustrate the advantage of using a catalyst of the type hereinbefore set forth, that is, cobalt promoted with titanium composited on a solid support, a series of experiments were performed evaluating various other types of catalysts. The reaction was effected by placing 0.2 moles of isophthalonitrile and from 0.65 to 1.05 moles of 2-methoxyethanol along with various amounts of catalyst into a glass liner for reaction in a rotating autoclave. The autoclave was then sealed and pressured to 400 psig with hydrogen and, in two instances, ammonia. The autoclave was then heated to a temperature of from 100° to 150° C. and maintained thereat for a period of three hours. At the end of this period heating was discontinued and after the autoclave had returned to room temperature the excess pressure was vented, the reaction product was separated from the catalyst by filtration and subjected to high pressure liquid chromotographic analysis. The results of these experiments are set forth in Table I below:

TABLE I
CATALYSTS EVALUATED FOR THE REDUCTION OF IPN TO MXDA

| Experiment | Reactants (moles) | | | Catalyst | | Pressure (psig) | Time (hours) | Temperature (°C.) | Conversion | Selectivity | Yield (wt. %) | | | |
|---|---|---|---|---|---|---|---|---|---|---|---|---|---|---|
| | $IPN^a$ | $Solvent^b$ | Ammonia | Type | Amount | | | | | | $^a IPN$ | $^h MBA$ | $^i MXDA$ | $^j Others$ |
| A | 0.2 | 1.05 | — | $^c$Co/XN1010 | 10 g. | 400 | 3 | 100 | 100 | 18 | — | 65 | 18 | 17 |
| B | 0.2 | 1.05 | — | 5 wt. % Pd/C | 1 g. | 400 | 3 | 100 | 100 | 62 | — | 11 | 62 | 27 |
| C | 0.2 | 1.05 | — | 5 wt. % Rh/C | 1 g. | 400 | 3 | 100 | 100 | 1 | — | 3 | 1 | 96 |
| D | 0.2 | 0.65 | 4.7 | $^d$R-S (16 mesh) | 10 g. | 400 | 3 | 100 | 59 | 0 | 41 | 4 | — | 55 |
| E | 0.2 | 0.65 | 0.4 | $^e$Ni/kiel. | 10 g. | 400 | 3 | 100 | 0 | 0 | 100 | — | — | — |
| F | 0.2 | 0.65 | — | $^f$Co/γ Al$_2$O$_3$ | 5 g. | 400 | 3 | 100 | 0 | 0 | 100 | — | — | — |
| G | 0.2 | 0.79 | — | 5 wt. % Ru/C | 1 g. | 400 | 3 | 150 | 100 | 3 | 0 | 3 | 2.5 | 94.5 |
| H | 0.2 | 0.79 | — | 5 wt. % Pt/C | 1 g. | 400 | 3 | 150 | 0 | 0 | 100 | — | — | — |
| I | 0.2 | 1.05 | — | $^g$Re/Cdo on Al$_2$O$_3$ | 3 g. | 400 | 3 | 150 | 100 | 1.4 | 0 | 45 | 1.4 | 53.6 |
| | | | | 5 wt. % Pd/C | 1 g. | 800 | 2 | 150 | | | | | | |

$^a$Isophthalonitrile;
$^b$2-Methoxyethanol;
$^c$Cobalt exchanged onto XN1010 cationic resin manufactured by Rohm and Haas;
$^d$Silica/alumina base containing 0.4 wt. % platinum sulfided and ground to 16 mesh;
$^e$60 wt. % nickel on kieselguhr clay pellets;
$^f$60 wt. % cobalt on gamma alumina;
$^g$1 wt. % Rhenium and 7 wt. % cadmium oxide on alumina;
$^h$m-Methylbenzylamine;
$^i$m-Xylylenediamine;
$^j$Heavies, 2°, 3° amines resulting from condensation of 2 or more MXDA's.

It will be noted that none of the above catalysts were effective in producing the desired amount of m-xylylenediamine, that is, a yield of over 90%.

EXAMPLE II

In a second series of experiments, anhydrous ammonia was utilized along with the various catalysts set forth in Example I above. These experiments were performed in a manner similar to that hereinbefore set forth, that is, 0.2 moles of isophthalonitrile and the catalysts were placed in the glass liner of a rotating autoclave along with 2-methoxyethanol. The autoclave was sealed and anhydrous ammonia charged in followed by hydrogen until pressures ranging from 400 to 800 psig were reached. The autoclave was then heated to temperature ranging from 80° to 150° C. for periods of time ranging from 3 to 5 hours. The results of these experiments are set forth in Table II below.

Again, it will be noted that the use of ammonia along with these catalysts did not result in the obtention of the desired yield of m-xylylenediamine.

TABLE II

| Experiment | Reactants (moles) | | | Catalyst | | Pressure (psig) | Time (hours) | Temperature °C. | Conversion | Selectivity | Yields (wt. %) | | | |
|---|---|---|---|---|---|---|---|---|---|---|---|---|---|---|
| | $IPN^b$ | $Solvent^c$ | $NH_3^a$ | Type | Amount | | | | | | $IPN^b$ | $MBA^f$ | $MXDA^g$ | $Other^h$ |
| A | 0.2 | 0.79 | 0.4 | 5 wt. % Pd/C | 1 g. | 400 | 5 | 125 | 85 | 2 | 15 | 17 | 2 | 6 |
| B | 0.2 | 0.79 | 0.4 | 5 wt. % Bh/C | 1 g. | 400 | 3 | 100 | 100 | 88 | — | 3 | 88 | 9 |
| C | 0.2 | 1.05 | 0.6 | R-5 (16 mesh)$^e$ | 10 g. | 400 | 5 | 100 | 91 | 10 | 9 | 4 | 9 | 78 |
| D | 0.2 | 1.05 | 0.4 | Ni/Kiel.$^d$ | 10 g. | 800 | 5 | 125 | 100 | 67 | — | — | 67 | 33 |
| E | 0.2 | 0.65 | 0.4 | 5 wt. % Ru/C | 1 g. | 400 | 3 | 100 | 0 | 0 | 100 | — | — | — |
| F | 0.2 | 1.05 | 0.4 | 5 wt. % Pt/C | 1 g. | 800 | 3 | 150 | 100 | 20 | — | 34 | 20 | 46 |

TABLE II-continued

| Ex-peri-ment | Reactants (moles) | | | Catalyst | | Pressure (psig) | Time (hours) | Temperature °C. | Conversion | Selectivity | Yields (wt. %) | | | |
|---|---|---|---|---|---|---|---|---|---|---|---|---|---|---|
| | IPN[b] | Solvent[c] | NH₃[a] | Type | Amount | | | | | | IPN[b] | MBA[f] | MXDA[g] | Other[h] |
| G | 0.2 | 1.05 | 0.6 | 5 wt. % Pd/C | 1 g. | 800 | 5 | 100 | 100 | 15 | — | 45 | 15 | 40 |

[a] Liquid, Matheson Gas Co;
[b] Isophthalonitrile;
[c] 2-Methoxyethanol;
[d] 60 wt. % Nickel on kieselguhr clay pellets;
[e] 0.4 wt. % Platinum on silica-alumina, sulfided and ground to 16 mesh;
[f] m-Methylbenzylamine;
[g] m-Xylylenediamine;
[h] Heavies, secondary, tertiary amines formed from the condensation of 2 or more MXDA units.

EXAMPLE III

In this example, the reduction of isophthalonitrile to the desired m-xylylenediamine was effected utilizing the catalyst of the present invention, that is, cobalt promoted with titanium composited on a solid support along with ammonia, the reaction being effected in the presence of a solvent comprising m-xylylenediamine. The experiments were effected by placing the catalyst comprising 60 wt. % of cobalt and 4 wt. % of titanium composited on kieselguhr along with the isophthalonitrile and m-xylylenediamine in the glass liner of a rotating autoclave. The autoclave was sealed, flushed with nitrogen, ammonia added, and hydrogen pressured in until an operating pressure of 1000 psig was reached. The autoclave was maintained at a temperature of 95° C. for a period of 8 hours following which heating was discontinued. After the autoclave had returned to room temperature, the excess pressure was vented and the reaction product was recovered by filtration from the catalyst. The catalyst and autoclave liner were rinsed with methanol which was added to the reaction product. After stripping the methanol, the product was analyzed by means of high pressure liquid chromatography.

The results of these experiments are set forth in Table III below:

TABLE III

| Experiment | Reactants (moles) | | | Catalyst | | Pressure (psig) | Time (hours) | Temperature (°C.) | Conversion | Selectivity | Yields (wt. %) | | | |
|---|---|---|---|---|---|---|---|---|---|---|---|---|---|---|
| | IPN[a] | Solvent[b] | NH₃[c] | Type | Amount | | | | | | IPN | MBA[d] | MXDA | Other[e] |
| A | 0.2 | 1 | 1.8 | Co/Ti | 10 g. | 1000 | 8 | 95 | 100 | 88 | — | — | 88 | 12 |
| B | 0.2 | 1 | 1.8 | Co/Ti[f] | 10 g. | 1000 | 8 | 95 | 100 | 94 | — | — | 94 | 6 |

[a] Isophthalonitrile;
[b] m-Xylylenediamine;
[c] Ammonia, anhydrous;
[d] Methylbenzylamine;
[e] "2° & 3°" oligomers m-xylylenediamine;
[f] Recycled.

It is to be noted from the above table that yields ranging from 88% to 94% of the desired m-xylylenediamine were obtained along with a 100% conversion of the isophthalonitrile, the remainder of the product comprising secondary and tertiary amines which had formed from the condensation of two or more m-xylylenediamine units.

It is therefore apparent that by utilizing the particular catalyst herein described along with ammonia in the liquid phase at a pressure not greater than 1000 psig and utilizing a xylylenediamine as the solvent for the reaction, it is possible to obtain attractive yields of the desired product.

EXAMPLE IV

To illustrate the advantages of using a catalyst comprising cobalt promoted with titanium when compared to cobalt promoted with zirconium in a recycle operation, 0.2 moles of isophthalonitrile, 1 mole of m-xylylenediamine and 3 grams of a catalyst comprising 60% by weight of cobalt composited on kieselguhr and promoted with 2% by weight of zirconium were placed in the glass liner of a rotating autoclave. The autoclave was sealed and pressured with nitrogen and hydrogen to an operating pressure of 1000 psig. The reaction was allowed to proceed for a period of 8 hours at the end of which time heating was discontinued and after the autoclave had returned to room temperature, the excess pressure was vented. The reaction product was separated from the catalyst and analyzed by high pressure liquid chromatography. This analysis disclosed that there had been a 100% conversion of the isophthalonitrile with a 96% yield of m-xylylenediamine.

The catalyst which had been recovered from this operation was recycled and utilized to treat 0.02 moles of isophthalonitrile in a manner identical in nature to the first run. The results at the end of the 8 hour period on the reaction product showed that there had been a drop to 88% yield of the desired m-xylylenediamine.

This 8% decrease in the yield of the desired product is contrasted to the results set forth in Table III above in which the experiment labeled "B" utilized the catalyst comprising cobalt promoted with titanium in a recycle operation under similar conditions. It is noted that the results showed that the use of the catalyst promoted with titanium not only maintained its activity but resulted in an increase of 6 wt. % of the desired m-xylylenediamine as compared to the decrease in a recycle operation when using the catalyst promoted with zirconium.

I claim as my invention:

1. A process for the preparation of a xylylenediamine which comprises treating a phthalonitrile with hydrogen at treating conditions in the presence of ammonia and a catalyst comprising cobalt promoted with titanium composited on a solid support, said treatment being effected in the presence of a solvent comprising a xylylenediamine and recovering the resultant xylylenediamine.

2. The process as set forth in claim 1 in which said reaction conditions include a temperature in the range of from about 80° to about 125° C. and a pressure not greater than 1000 pounds per square inch gauge.

3. The process as set forth in claim 3 in which said pressure is in a range of from about 900 to about 1000 pounds per square inch gauge.

4. The process as set forth in claim 1 in which the ammonia is present in a mole ratio of ammonia to phthalonitrile in a range of from about 5:1 to about 10:1 moles of ammonia per mole of phthalonitrile.

5. The process as set forth in claim 1 in which said titanium is present in said catalyst in an amount in the range of from about 1% to about 20% by weight of said catalyst.

6. The process as set forth in claim 1 in which said cobalt is present in said catalyst in an amount in the range of from about 40% to about 70% by weight of said catalyst.

7. The process as set forth in claim 1 in which said solid support is carbon.

8. The process as set forth in claim 1 in which said solid support is kieselguhr.

9. The process as set forth in claim 1 in which said solid support is silica.

10. The process as set forth in claim 1 in which said phthalonitrile is isophthalonitrile and said xylylenediamine is m-xylylenediamine.

11. The process as set forth in claim 10 in which said phthalonitrile is terephthalonitrile and said xylylenediamine is p-xylylenediamine.

12. The process as set forth in claim 10 in which said solvent comprises m-xylylenediamine.

13. The process as set forth in claim 11 in which said solvent comprises p-xylylenediamine.

* * * * *